United States Patent
Yoo et al.

(10) Patent No.: US 12,266,447 B2
(45) Date of Patent: Apr. 1, 2025

(54) METHOD AND SYSTEM FOR GENERATING MEDICAL PREDICTION RELATED TO BIOMARKER FROM MEDICAL DATA

(71) Applicant: LUNIT INC., Seoul (KR)

(72) Inventors: Donggeun Yoo, Seoul (KR); Jeong Hoon Lee, Seoul (KR); Kyunghyun Paeng, Seoul (KR)

(73) Assignee: LUNIT INC., Seoul (KR)

( * ) Notice: Subject to any disclaimer, the term of this patent is extended or adjusted under 35 U.S.C. 154(b) by 721 days.

(21) Appl. No.: 17/502,304

(22) Filed: Oct. 15, 2021

(65) Prior Publication Data

US 2022/0037024 A1    Feb. 3, 2022

Related U.S. Application Data

(63) Continuation of application No. PCT/KR2021/006034, filed on May 13, 2021.

(30) Foreign Application Priority Data

May 13, 2020 (KR) .................... 10-2020-0057256
May 13, 2021 (KR) .................... 10-2021-0062294

(51) Int. Cl.
*G16H 50/20* (2018.01)
*G06T 7/00* (2017.01)
*G16H 10/60* (2018.01)
*G16H 50/70* (2018.01)

(52) U.S. Cl.
CPC .......... *G16H 50/20* (2018.01); *G06T 7/0014* (2013.01); *G16H 10/60* (2018.01); *G16H 50/70* (2018.01); *G06T 2207/20084* (2013.01)

(58) Field of Classification Search
CPC ........ G16H 50/20; G16H 10/60; G16H 50/70; G16H 50/30; G06T 7/0014; G06T 2207/20084; G06N 20/00
USPC .......................................................... 705/2–3
See application file for complete search history.

(56) References Cited

U.S. PATENT DOCUMENTS

2019/0025308 A1 * 1/2019 Cummings ............ G16H 50/50

FOREIGN PATENT DOCUMENTS

| EP | 3293736 A1 * | 3/2018 | ............. A61B 5/055 |
| JP | 2019528426 A | 10/2019 | |
| KR | 1020160079127 A | 7/2016 | |
| KR | 1020200021082 A | 2/2020 | |

(Continued)

OTHER PUBLICATIONS

Crawford et al., "Incorporating biological structure into machine learning models in biomedicine", greenlab/biopriors-review@e869a1f, Oct. 14, 2019 (18 pages) (Year: 2019).*

(Continued)

*Primary Examiner* — Joy Chng
(74) *Attorney, Agent, or Firm* — Sughrue Mion, PLLC

(57) ABSTRACT

A method for generating a medical prediction related to a biomarker from medical data is provided, which includes obtaining medical data associated with a patient, determining a region of interest in the medical data, extracting one or more features associated with the medical data based on the region of interest, and generating a medical prediction for the patient based on the extracted one or more features.

18 Claims, 11 Drawing Sheets

(56) References Cited

FOREIGN PATENT DOCUMENTS

WO           2019169044 A1     9/2019
WO     WO-2019191123 A1 * 10/2019     ........... G16B 10/00

OTHER PUBLICATIONS

Jake Crawford, et al. "Incorporating biological structure into machine learning models in biomedicine", greenlab\biopriors-review@e869a1f, Oct. 14, 2019 (18 pages).
Translation of the International Search Report of PCT/KR2021/006034 dated Aug. 19, 2021.

* cited by examiner

METHOD AND SYSTEM FOR GENERATING MEDICAL PREDICTION RELATED TO BIOMARKER FROM MEDICAL DATA

CROSS-REFERENCE TO RELATED APPLICATIONS

This application is a continuation of International Application No. PCT/KR2021/006034 filed on May 13, 2021 which claims priority to Korean Patent Application No. 10-2020-0057256 filed on May 13, 2020 and Korean Patent Application No. 10-2021-0062294 filed on May 13, 2021, the entire contents of which are herein incorporated by reference.

TECHNICAL FIELD

The present disclosure relates to a method and a system for generating a medical prediction related to a biomarker from medical data, and more particularly, to providing a method and a system for extracting one or more features associated with medical data associated with a patient based on a region of interest in the medical data and generating a medical prediction for the patient based on the extracted one or more features.

BACKGROUND

In recent years, machine-learning technology centered on deep learning is attracting increasing attention for its results that exceed the performance of existing methods in analyzing various types of data such as pictures, voices, texts, and the like. This machine learning technology is introduced and utilized in various fields thanks to the inherent scalability and flexibility of the technology itself. In addition, the machine learning technology is also actively used in the field where it is necessary to discover new materials or predict outcomes that are difficult for humans to predict. In particular, medical field is one of the fields where the machine learning technology is actively incorporated to develop diagnosis assistance systems and the like.

The diagnostic assistance systems and the like are able to diagnose a specific disease or predict a responsiveness to a specific drug in advance in consideration of some factors included in the medical data associated with a patient, based on medical knowledge such as medically established causal relationship and the like. In other words, the systems can help reduce overall medical costs by diagnosing diseases early and avoiding additional tests. However, in diagnosing a specific disease or predicting responsiveness to a specific drug, there may be many factors in medical data of which medical causal relationship is not yet known. Therefore, according to the related art, there is a possibility of missing certain factors that are important for the diagnosis of a specific disease or the prediction of the responsiveness to a specific drug, but are not yet established medically.

DISCLOSURE

Technical Problem

In order to solve the problems described above, the present disclosure provides a method and a system for generating a medical prediction associated with a biomarker from medical data.

Technical Solution

The present disclosure may be implemented in various ways, including a method, an apparatus (system), a computer readable storage medium storing instructions, or a computer program.

A method for generating a medical prediction related to a biomarker from medical data according to an embodiment may include obtaining medical data associated with a patient, determining a region of interest in the medical data, extracting one or more features associated with the medical data based on the region of interest, and generating a medical prediction for the patient based on the extracted one or more features.

In an embodiment, the determining may include determining the region of interest to extract at least one of an anatomical feature, a geometric feature, or a histological feature from the medical data.

In an embodiment, the determining the region of interest to extract at least one of the anatomical feature, the geometric feature, or the histological feature may include determining the region of interest in the medical data by using a feature extraction model that is trained to extract at least one of the anatomical feature, the geometric feature, or the histological feature from the medical data.

In an embodiment, the medical data may include genomic data, and the determining the region of interest may include determining at least one gene group having a characteristic same as or similar to a characteristic included in the genomic data by using a database related to an interpretation of the genomic data, and determining the region of interest in the genomic data using the determined at least one gene group.

In an embodiment, the medical data may include first and second medical data belonging to categories different from each other, and the extracting the one or more features may include extracting one or more features associated with the second medical data based on the region of interest determined from the first medical data.

In an embodiment, the extracted one or more features may include one or more first features associated with the medical data, the method may further include extracting one or more second features associated with the medical data from at least a portion of a region other than the region of interest, and the generating may include generating a medical prediction for the patient based on the one or more first features and the one or more second features.

In an embodiment, the generating the medical prediction based on the one or more first features and the one or more second features may include performing normalization of each of the one or more first features and the one or more second features, combining the normalized one or more first features and the normalized one or more second features to generate one or more third features, and generating the medical prediction for the patient based on the generated one or more third features.

In an embodiment, the medical data may include at least one of medical image data related to imaging medicine, tissue image data, genomic data, or biological data.

In an embodiment, the generating may include generating a prediction result for at least one of a treatment method, a therapeutic drug, or a duration of treatment related to a patient's disease.

In an embodiment, the generating may include generating a prediction result for at least one of a therapeutic responsiveness of the patient or a survival rate of the patient for at least one of a specific treatment method or a specific therapeutic drug.

In an embodiment, the method may further include indicating at least one of the determined region of interest, the extracted one or more features, or the generated medical prediction on the medical data.

In an embodiment, the method may further include outputting the generated medical prediction.

A computer program is provided, which is stored on a computer-readable recording medium for executing, on a computer, a method for generating a medical prediction related to a biomarker from medical data described above according to an embodiment.

An information processing system according to an embodiment is provided, including a memory storing one or more instructions, and a processor configured to execute the stored one or more instructions to obtain medical data associated with a patient, determine a region of interest in the medical data, extract one or more features associated with the medical data based on the region of interest, and generate a medical prediction for the patient based on the extracted one or more features.

Advantageous Effects

According to some embodiments of the present disclosure, it is possible to find a region, element and/or factor of medical data for which the medical causal relationship has not yet been revealed, but has an important influence on the medical prediction. For example, with a machine learning model that is trained using a plurality of medical data-prediction correct pairs, an important region for performing the medical prediction can be indirectly found.

According to some embodiments, a feature can be extracted from a region other than the region of interest in the medical data. Since the regions other than the region of interest defined based on an already established medical causal relationship or the region of interest defined using a machine learning model may also include a significant feature for performing the medical prediction, the features extracted in this way (that is, features extracted from the non-region of interest) can be helpful for the medical prediction.

According to some embodiments, the effects described above can bring about increased variety of medical prediction and also the improved accuracy.

The effects of the present disclosure are not limited to the effects described above, and other effects not described will be able to be clearly understood by those of ordinary skill in the art (hereinafter, referred to as "those skilled in the art") from the description of the claims.

BRIEF DESCRIPTION OF THE DRAWINGS

Embodiments of the present disclosure will be described with reference to the accompanying drawings described below, where similar reference numerals indicate similar components, but not limited thereto.

DETAILED DESCRIPTION

Figure 1:
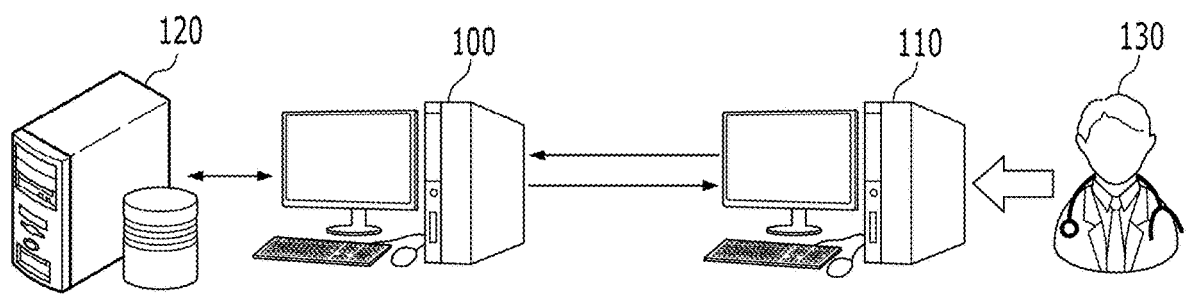
FIG. 1 is an exemplary configuration diagram illustrating a system in which an information processing system generates a medical prediction related to a biomarker from medical data according to an embodiment.

Hereinafter, specific details for the practice of the present disclosure will be described in detail with reference to the accompanying drawings. However, in the following description, detailed descriptions of well-known functions or configurations will be omitted when it may make the subject matter of the present disclosure rather unclear.

In the accompanying drawings, the same or corresponding elements are assigned the same reference numerals. In addition, in the following description of the embodiments, duplicate descriptions of the same or corresponding components may be omitted. However, even if descriptions of elements are omitted, it is not intended that such elements are not included in any embodiment.

Advantages and features of the disclosed embodiments and methods of accomplishing the same will be apparent by referring to embodiments described below in connection with the accompanying drawings. However, the present disclosure is not limited to the embodiments disclosed below, and may be implemented in various different forms, and the present embodiments are merely provided to make the present disclosure complete, and to fully disclose the scope of the invention to those skilled in the art to which the present disclosure pertains.

The terms used herein will be briefly described prior to describing the disclosed embodiments in detail. The terms used herein have been selected as general terms which are widely used at present in consideration of the functions of the present disclosure, and this may be altered according to the intent of an operator skilled in the art, conventional practice, or introduction of new technology. In addition, in a specific case, a term is arbitrarily selected by the applicant, and the meaning of the term will be described in detail in a corresponding description of the embodiments. Therefore, the terms used in the present disclosure should be defined based on the meaning of the terms and the overall contents of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. As used throughout the description, when one part is referred to as "comprising" (or "including" or "having") other elements, the part can comprise (or include or have) only those elements or other elements as well as those elements unless specifically described otherwise.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to reproduce one or more processors. Accordingly, as an example, the "module" or "unit" may include components such as software components, object-oriented software components, class components, and task components, and at least one of processes, functions, attributes, procedures, subroutines, program code segments of program code, drivers, firmware, micro-codes, circuits, data, database, data structures, tables, arrays, or variables. Furthermore, functions provided in the components and the "modules" or "units" may be combined into a smaller number of components and "modules" or "units", or further divided into additional components and "modules" or "units."

According to an embodiment, the "module" or "unit" may be implemented as a processor and a memory. The "processor" should be interpreted broadly to encompass a general-purpose processor, a central processing unit (CPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination of processing devices, e.g., a combination of a DSP and a microprocessor, a plurality of microprocessors, one or more microprocessors in conjunction with a DSP core, or any other combination of such configurations. In addition, the "memory" should be interpreted broadly to encompass any electronic component capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and so on. The memory is said to be in electronic communication with a processor if the processor can read information from and/or write information to the memory. The memory integrated with a processor is in electronic communication with the processor.

In the present disclosure, the "system" may refer to at least one of a server device and a cloud device, but not limited thereto. For example, the system may include one or more server devices. As another example, the system may include one or more cloud devices. As another example, the system may be configured together with both a server device and a cloud device and operated.

In the present disclosure, "target data" may refer to any data or data item that can be used for training of a machine learning model, and may include, for example, data representing an image, data representing voice or voice characteristics, and the like, but is not limited thereto. In addition, the target data may be tagged with label information through an annotation task.

In the present disclosure, "medical data" may refer to any data to be analyzed for diagnosis or prediction of a condition of a living organism (e.g., the human body), and/or prevention or treatment of a disease of the living organism, and the like. For example, the "medical data" may include tissue, image, genomic data, and the like of the living organism. As another example, the "medical data" may include an image (e.g., pathology slide image) obtained by capturing a pathology slide that is fixed and stained through a series of chemical processes to observe the tissue and the like of the living organism under a microscope. In this case, the "medical data" may include information on cells, tissues, and/or structures in the living organism. As still another example, the "medical data" includes clinical or histological label information of the living organism (e.g., whether malignant or benign, recurrence or non-recurrence, metastasis or non-metastasis, response or non-response to specific anticancer drug, side effect or no side effect to drugs, effect or no effect of specific surgery, prognosis, quality of life, pain, and the like).

In the present disclosure, an "image" may refer to a "picture", and conversely, the "picture" may refer to the "image". That is, the "image" and the "picture" may be used interchangeably herein. In addition, in the present disclosure, "image data" may include medical data in the form of an image, that is, medical image data.

In the present disclosure, a "region of interest" may refer to, in the medical data, at least a certain region that is a target of analysis to perform a specific medical prediction (e.g., prediction of responsiveness to a drug, side effect or no side effect, prognosis, and the like). For example, the "region of interest" may include a region that corresponds to a specific medical prediction by a medical causal relationship, a region that includes a target item to be analyzed for a specific medical prediction (e.g., a biological element, a factor, and the like), and the like. In an embodiment, regarding the medical data in the form of an image, the "region of interest" may include pixels of at least some of a plurality of pixels of the medical data. The region of interest in the medical data in the form of an image may include a region such as a specific lesion, a site, an organ, a tissue, and the like. In another embodiment, regarding the genomic data, the "region of interest" may include at least some feature points of the factors (or elements) such as mutations, genes, genome structures, and the like, that are targeted to be analyzed to perform a medical prediction.

In the present disclosure, a "machine learning model" and/or an "artificial neural network model" may include any model that is used for inferring an answer to a given input. According to an embodiment, the machine learning model may include an artificial neural network model including an input layer (layer), a plurality of hidden layers, and output layers. In an example, each layer may include a plurality of nodes. For example, the machine learning model may be trained to infer label information for at least certain region (e.g., region of interest) of medical data. In this case, the label information generated through the annotation task may be used to train the machine learning model. In addition, the machine learning model may include weights associated with a plurality of nodes included in the machine learning model. In an example, the weight may include an any parameter associated with the machine learning model.

In the present disclosure, "training" may refer to any process of changing the weights associated with the machine learning model using at least a portion of the region of the medical data and label information (e.g., predictive correct answer). According to an embodiment, the training may refer to a process of changing or updating weights associated with the machine learning model through one or more of forward propagation and backward propagation of the machine learning model using at least one patch and the label information.

In the present disclosure, the "label information" is correct answer information of the data sample information, which is obtained as a result of the annotation task. The label or label information may be used interchangeably with terms such as annotation, tag, and so on as used in the art. In the present disclosure, the "annotation" may refer to an annotation work and/or annotation information (e.g., label information, and the like) determined by performing the annotation work. In the present disclosure, the "annotation information" may refer to information for the annotation work and/or information generated by the annotation work (e.g., label information).

In the present disclosure, the "target item" may refer to data/information, a region, an object, and the like that is targeted to be detected in the medical data. According to an embodiment, the target item may include a target to be detected from the medical data for diagnosis, treatment, prevention, or the like of a disease (e.g., cancer). For example, the "target item" may include a specific cell (e.g., a cancer cell, an immune cell, and the like), a specific region (e.g., a cancerous region, a specific organ region), and the like in medical image data. As another example, the "target item" may include a specific nucleotide sequence in genomic data, a gene expression level, a phenotype, and the like.

In the present disclosure, "instructions" may refer to one or more instructions grouped based on functions, which are the components of a computer program and executed by the processor.

In the present disclosure, a "user" may refer to a person who uses a user terminal. For example, the user may include an annotator who performs the annotation work. As another example, the user may include a doctor, a patient, and the like provided with a medical prediction result (e.g., a prediction result as to whether or not the patient responds to immune anticancer drugs). In addition, the user may refer to the user terminal, or conversely, the user terminal may refer to the user. That is, the user and the user terminal may be interchangeably used herein.

FIG. 1 is an exemplary configuration diagram illustrating a system in which an information processing system 100 generates a medical prediction related to a biomarker from medical data according to an embodiment. As illustrated, a system that generates a medical prediction related to a biomarker from medical data may include the information processing system 100, a user terminal 110, and a storage system 120. In an example, the information processing system 100 may be configured to be connected to each of the user terminal 110 and the storage system 120 for communication. While FIG. 1 illustrates one user terminal 110, the present disclosure is not limited thereto, and in an exemplary configuration, a plurality of user terminals 110 may be connected to the information processing system 100 for communication. In addition, while the information processing system 100 is shown as one computing device in FIG. 1, the present disclosure is not limited thereto, and the information processing system 100 may be configured to process information and/or data in a distributed manner through a plurality of computing devices. In addition, while the storage system 120 is shown as a single device in FIG. 1, the present disclosure is not limited thereto, and the system may be configured with a plurality of storage devices or as a system that supports a cloud. In addition, respective components of the system for generating a medical prediction related to a biomarker from medical data illustrated in FIG. 1 represent functional components that can be divided on the basis of functions, and in an actual physical environment, a plurality of components may be implemented as being incorporated with each other.

The information processing system 100 and the user terminal 110 are any computing devices that are used to generate a medical prediction related to a biomarker from medical data and provide the same. In an example, the computing device may refer to any type of device equipped with a computing function, and may be a notebook, a desktop, a laptop, a server, a cloud system, and the like, for example, but is not limited thereto.

The information processing system 100 may receive medical data associated with a patient. For example, the information processing system 100 may receive the medical data associated with the patient from the storage system 120 and/or the user terminal 110. The information processing system 100 may determine a region of interest from the obtained medical data. For example, the information processing system 100 may determine the region of interest to extract at least one of an anatomical feature, a geometric feature, or a histological feature from the medical data.

Then, the information processing system 100 may extract one or more features (e.g., one or more first features) associated with the medical data based on the region of interest, and generate a medical prediction for the patient based on the extracted one or more features. Additionally or alternatively, the information processing system 100 may extract one or more second features associated with the medical data from at least a portion of the region (e.g., a non-region of interest) other than the region of interest. In this case, the information processing system 100 may generate a medical prediction for the patient based on the one or more first features and the one or more second features.

The information processing system 100 may output the generated medical prediction for the patient. For example, the information processing system 100 may transmit the generated medical prediction for the patient to the user terminal 110, and the user terminal 110 may display the medical prediction for the patient received from the information processing system 100 on a display device. For example, the user terminal 110 may receive the medical data and/or the medical prediction result indicating at least one of the region of interest, the one or more features, or the medical prediction from the information processing system 100, and may display the same on the display device. Accordingly, a user 130 (e.g., a doctor, a patient, and the like) may receive the medical prediction (that is, the prediction result) for the patient through the user terminal 110.

The storage system 120 is a device or cloud system that stores and manages medical data and various data associated with the machine learning model for generating a medical prediction related to a biomarker from medical data. For efficient data management, the storage system 120 may store and manage various types of data using a database. In this example, the various data may include any data associated with the machine learning model, and include, for example, a file of the target data, meta information of the target data, label information for the target data as a result of the annotation work, data related to the annotation work, a machine learning model (e.g., an artificial neural network model), and the like, but are not limited thereto. While FIG. 1 shows the information processing system 100 and the storage system 120 as separate systems, the present disclosure is not limited thereto, and they may be incorporated into one system.

Figure 2:
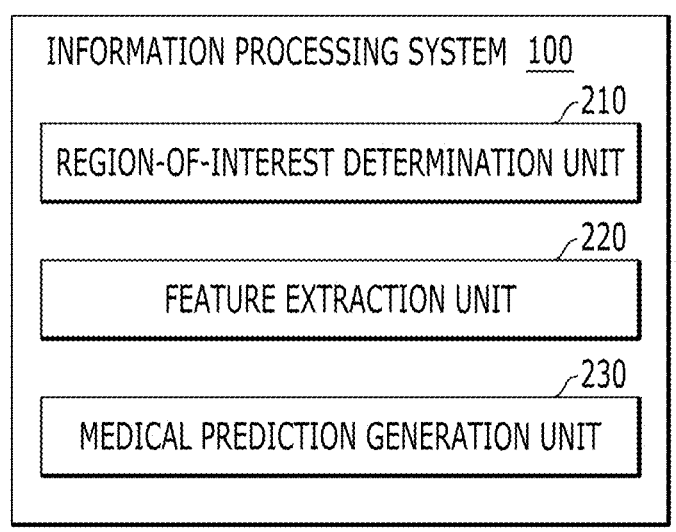
FIG. 2 is a block diagram illustrating an internal configuration of the information processing system according to an embodiment.

FIG. 2 is a block diagram illustrating an internal configuration of the information processing system 100 according to an embodiment. According to an embodiment, in order to generate a medical prediction related to a biomarker from the medical data, as illustrated, the information processing system 100 may include a region-of-interest determination unit 210, a feature extraction unit 220, and a medical prediction generation unit 230. Respective components of the information processing system 100 illustrated in FIG. 2 represent functional components that can be divided on the basis of functions, and in an actual physical environment, a plurality of components may be implemented as being incorporated with each other.

The region-of-interest determination unit 210 may obtain medical data associated with the patient and determine a region of interest from the medical data. In an embodiment, the region-of-interest determination unit 210 may determine a region of interest to extract at least one of the anatomical feature, the geometric feature, or the histological feature from the medical data. For example, the region-of-interest determination unit 210 may determine the region of interest in the medical data using a feature extraction model trained to extract at least one of the anatomical feature, the geometric feature, or the histological feature from the medical data. In another embodiment, when the medical data corresponds to the genomic data, the region-of-interest determination unit 210 may use a database related to the interpretation of the genomic data to determine at least one gene group having the characteristics same as or similar to those included in the genomic data. Then, the region-of-interest determination unit 210 may use the determined at least one gene group to determine a region of interest from the genomic data. In this example, the genomic data may include DNA mutation data, structure data, expression data of RNA, protein, and the like, epigenomic data such as methylation and the like, liquid biopsy analysis data, and the like, but is not limited thereto.

The feature extraction unit 220 may extract one or more features (e.g., one or more first features) associated with the medical data based on the region of interest. In an embodiment, when the medical data includes the first and second medical data belonging to categories different from each other, the feature extraction unit 220 may extract one or more features associated with the second medical data based on the region of interest determined from the first medical data. Additionally or alternatively, the feature extraction unit 220 may extract one or more features (e.g., one or more second features) associated with the medical data from at least a portion of the region other than the region of interest. Additionally or alternatively, the feature extraction unit 220 may perform normalization of each of the features (that is, one or more first features) extracted from the region of interest and the features (that is, one or more second features) extracted from at least a portion of the region other than the region of interest, and combine one or more normalized first features and one or more normalized second features to generate one or more third features.

The medical prediction generation unit 230 may generate a medical prediction for the patient based on the one or more extracted features. In an embodiment, the medical prediction generation unit 230 may generate the medical prediction for the patient based on the one or more first features and the one or more second features extracted by the feature extraction unit 220. For example, the medical prediction generation unit 230 may generate the medical prediction for the patient based on the one or more third features generated by the feature extraction unit 220.

In FIG. 2, the information processing system 100 includes the region-of-interest determination unit 210, the feature extraction unit 220, and the medical prediction generation unit 230, but is not limited thereto, and some components may be omitted or other components may be added. In an embodiment, the information processing system 100 may further include an output unit (not illustrated), and the output unit may output the generated medical prediction. In addition, while FIG. 2 illustrates that the region-of-interest determination unit 210, the feature extraction unit 220, and the medical prediction generation unit 230 are included in the information processing system 100, the present disclosure is not limited thereto, and these components may be included in other devices (e.g., external device and/or user terminal). In another embodiment, these components may be distributed in any combination by a plurality of any devices (e.g., the information processing system 100, the user terminal 110, and the like).

Figure 3:
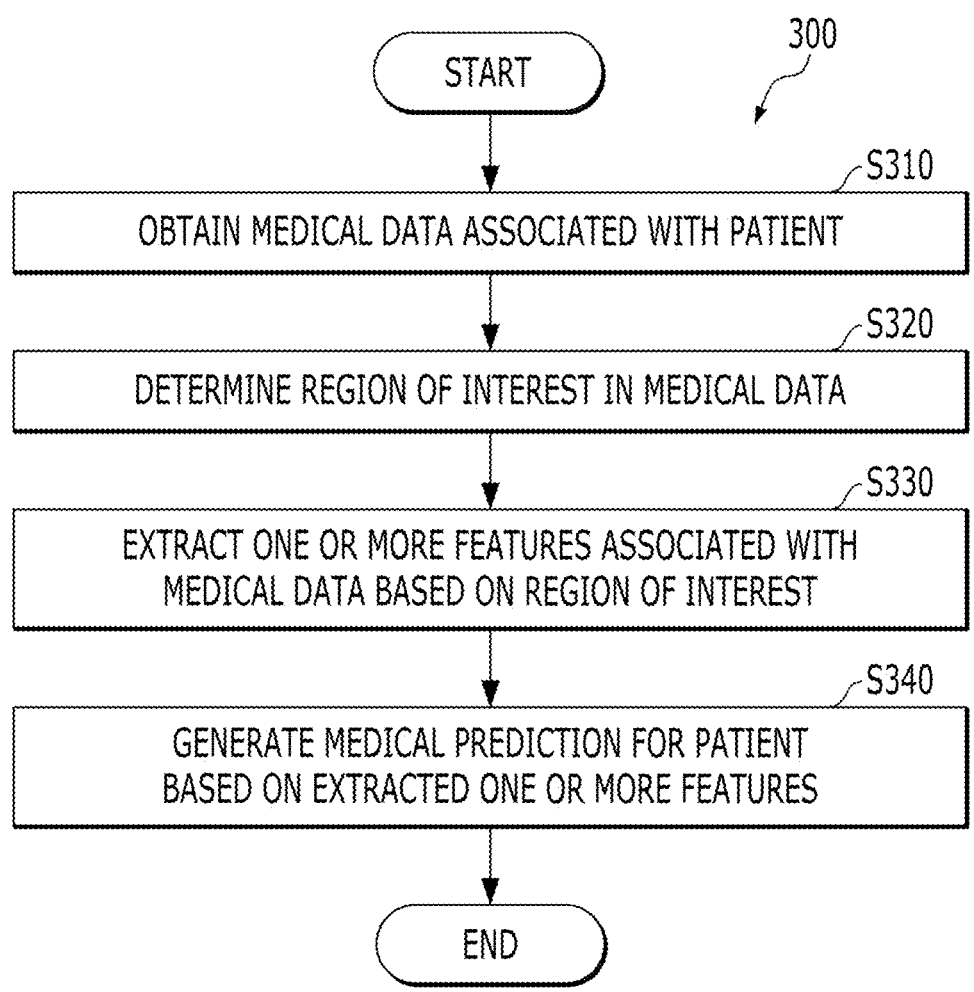
FIG. 3 is a flowchart illustrating a method for generating a medical prediction according to an embodiment.

FIG. 3 is a flowchart illustrating a method 300 for generating a medical prediction according to an embodiment. In an embodiment, the method 300 for generating a medical prediction may be performed by a processor (e.g., at least one processor of the information processing system and/or at least one processor of the user terminal). The method 300 for generating a medical prediction may be initiated by the processor obtaining medical data associated with the patient, at S310. In this example, the medical data may include at least one of medical image data associated with medical imaging, tissue image data, genomic data, or biological data. For example, the medical data may include at least one of radiographic image data such as X-ray, CT, MRI images, and the like, tissue image data such as digital pathology and the like (e.g., H&E staining image, IHC slide image, and the like), genomic data including multi-omics data, and biological data. Additionally or alternatively, the medical data may include data of different modalities obtained from the patient.

The processor may determine the region of interest from the medical data, at S320. In an embodiment, the processor may determine the region of interest to extract at least one of the anatomical feature, the geometric feature, or the histological feature from the medical data. For example, the processor may determine the region of interest in the medical data using a feature extraction model trained to extract at least one of the anatomical feature, the geometric feature, or the histological feature from the medical data. In another embodiment, when the medical data corresponds to the genomic data, the processor may use the database related to the interpretation of the genomic data to determine at least one gene group having the characteristics same as or similar to those included in the genomic data, and use the determined at least one gene group to determine the region of interest from the genomic data.

Then, the processor may extract one or more features (e.g., one or more first features) associated with the medical data based on the region of interest, at S330. In an embodiment, when the medical data includes the first and second medical data belonging to categories different from each other, the processor may extract one or more features associated with the second medical data based on the region of interest determined from the first medical data. Additionally or alternatively, the processor may extract a feature (e.g., one or more second features) associated with the medical data from at least a portion of the region other than the region of interest.

Then, the processor may generate a medical prediction for the patient based on the extracted one or more features, at S340. In an embodiment, the processor may generate a prediction result for at least one of a treatment method, a therapeutic drug, or a treatment period for the patient's disease. In another embodiment, the processor may generate a prediction result for at least one of the patient's therapeutic responsiveness or the patient's survival rate (e.g., treatability or survivability) for at least one of a specific treatment method or a specific therapeutic drug. In another embodiment, the processor may indicate at least one of the determined region of interest, the extracted one or more features, or the generated medical prediction in the medical data. Additionally, the processor may output the generated medical prediction.

Figure 4:
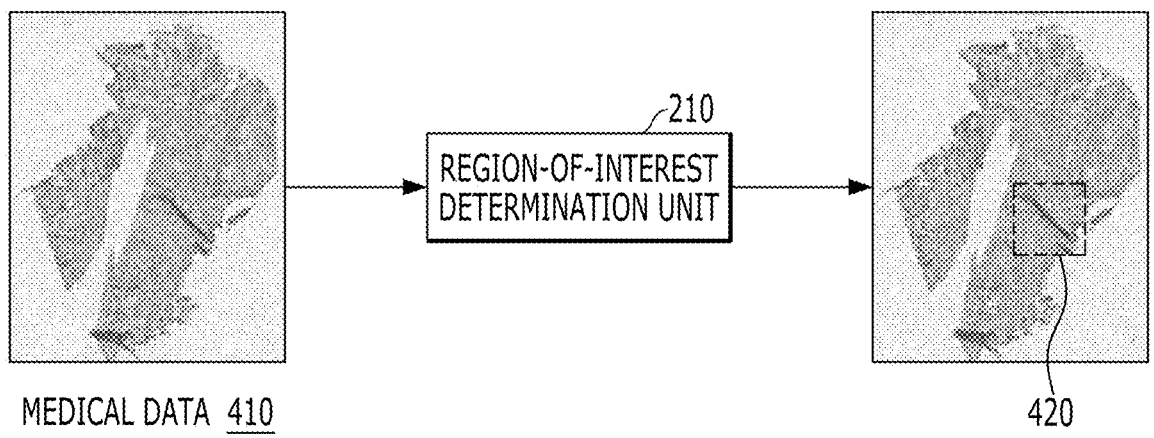
FIG. 4 is a diagram illustrating an example of determining a region of interest in medical data according to an embodiment.

FIG. 4 is a diagram illustrating an example of determining a region of interest 420 from medical data 410 according to an embodiment. The medical data may have regions that are not associated with the biomarker for performing a medical prediction. These non-associated regions may act as noise in determining the biomarker from a small amount of data. Accordingly, a biomarker with higher accuracy may be determined through the process of extracting the region of interest.

For example, for a biomarker for predicting response to a drug or treatment, it may be important to intensively analyze the abnormal region rather than the normal region. That is, in the case of a radiographic image, it may be important to regions around the lesion region rather than the entire regions. Likewise, in the case of a tissue image, it may be important to analyze the regions around the cancer or to analyze the distribution of specific cells in the regions around the cancer, not the entire region.

In order to perform a medical prediction, it may be important to determine, in the medical data, the region that requires intensive analysis as described above, that is, the region of interest. In an embodiment, as illustrated, the region-of-interest determination unit 210 may receive the medical data 410 (e.g., a pathology slide image) associated with the patient, and determine the region of interest 420 (e.g., at least a portion of the region within the pathological slide image) in the received medical data 410. For example, the region-of-interest determination unit 210 may determine, in the radiographic image, a specific lesion region, a radiologic finding region, a specific anatomical region, and/or a specific organ region as the region of interest. As another example, the region-of-interest determination unit 210 may determine a specific tissue in the tissue image as a region of interest.

In an embodiment, the region-of-interest determination unit 210 may determine a region of interest to extract at least one of the anatomical feature, the geometric feature, or the histological feature from the medical data. The anatomical feature, the geometric feature and/or the histological feature may include significant features to perform a medical prediction. The region of interest to extract the significant feature to perform a medical prediction may be directly defined by the user. For example, in the case of a pathological tissue image, the user may define a cancer stroma region and/or a cancer epithelium region as the region of interest for predicting a response to an anticancer drug with respect to lung cancer. As another example, in the case of a radiographic image, the user may define a region with lung cancer as the region of interest for predicting a response to an anticancer drug.

As described above, as the user defines a region including important factors for which a causal relationship was already medically established with respect to a prediction target (e.g., in predicting a response to an anticancer drug, and the like) as a region of interest, the region-of-interest determination unit 210 may determine a region corresponding to the region of interest defined by the user from the obtained medical data. On the other hand, there can be many factors, which are important to the accuracy of predicting biomarkers, but not medically known yet. Therefore, when the region of interest is defined based on only the important factors for which the causal relationship was already established medically, other important factors that are not yet medically established may be missed. For example, in predicting a response to an anticancer drug with respect to a lung cancer in the radiographic image, there is no medically established causal relationship as to whether only the "lung cancer region" would suffice, or the "location information of the lung where the lung cancer occurred" would also be necessary, but the "location information of the lung where the lung cancer occurred" may correspond to an important factor for predicting a response to the anticancer drug with respect to the lung cancer. Therefore, it is necessary to define the regions that may be important factors for the biomarkers as the regions of interest, even for the regions for which the causal relationship has not been medically established.

Accordingly, the region-of-interest determination unit 210 may use the feature extraction model (e.g., the machine learning model) trained to extract at least one of the anatomical feature, the geometric feature, or the histological feature from the medical data to determine the region of interest in the medical data. For example, the region-of-interest determination unit 210 may use the feature extraction model that is trained based on a plurality of medical data-predicted correct answer pairs to determine the region of interest in the medical data. In this example, the plurality of medical data may include the medical data itself and/or one or more features extracted from the medical data (e.g., a vector indicating a feature, and the like). In addition, the predicted correct answers may include a clinical/histological predictive correct value of the patient.

The region-of-interest determination unit 210 may use the feature extraction model to define, as the region of interest, a region having a significant influence (e.g., the greatest influence and/or influence equal to or greater than a threshold) on extracting at least one of the anatomical feature, the geometric feature, or the histological feature from the medical data. That is, the region-of-interest determination unit 210 may automatically define the region of interest using the machine learning model. For example, based on the plurality of medical data-predicted correct answer pairs, the region-of-interest determination unit 210 may extract a region that has a great influence on the prediction answer for each of the plurality of medical data by using the supervised machine learning model and define at least some of the extracted regions as the region of interest. For example, in predicting a response to an anticancer drug by inputting a radiographic image to the machine learning model, when a lung lymph node region of the radiographic image has a great influence on predicting the response to the anticancer drug, the region-of-interest determination unit 210 may define the lymph node of the lung as the region of interest. When both the region of interest defined by the user and the region of interest defined by the machine learning model are considered, the predictive performance of the biomarker may be improved.

The region-of-interest determination unit 210 may determine the region of interest defined as described above (e.g., the region of interest defined by the user and/or the region of interest defined by the machine learning model) from the obtained medical data associated with the patient. For example, the region-of-interest determination unit 210 may determine (or extract) the region of interest from the obtained medical data associated with the patient by using the region of interest determination model. In this case, the region of interest-determining model may correspond to a model that is trained based on the training medical data and the label information on the region of interest in the training medical data. In this case, the label information for the region of interest in the training medical data may be generated and/or received by the user's annotation task.

Figure 5:
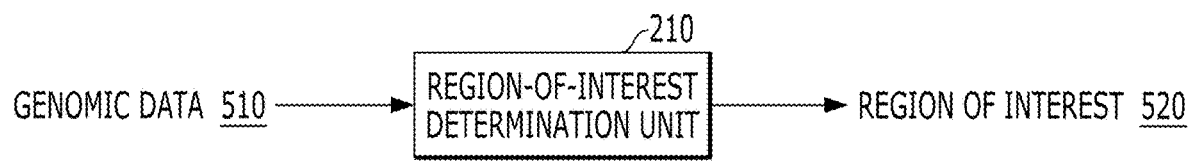
FIG. 5 is a diagram illustrating an example of determining a region of interest in genomic data according to an embodiment.

FIG. 5 is a diagram illustrating an example of determining a region of interest 520 from genomic data 510 according to an embodiment. As illustrated, the region-of-interest determination unit 210 may obtain the genomic data 510 associated with the patient as the medical data associated with the patient. The factors used in the genomic data may include mutations in DNA, gene expression values corresponding to RNA, epigenetic factors, expression values of proteomic bodies, microbiome existing in the body, and the like. Additionally or alternatively, the genomic data may include external data describing a biological characteristic associated with a genetic factor. The region-of-interest determination unit 210 may determine the region of interest (e.g., a feature point) from the genomic data. For example, the region-of-interest determination unit 210 may determine the region of interest (that is, a feature point) for a mutation, a gene, or a structure of a genome from the genomic data. Additionally or alternatively, the region-of-interest determination unit 210 may perform the method described with reference to FIG. 4 with respect to the genomic data to determine the region of interest (that is, a feature point) from the genomic data.

In an embodiment, the region-of-interest determination unit 210 may use at least one gene group to determine the region of interest from the genomic data. To this end, the region-of-interest determination unit 210 may use a database related to the interpretation of the genomic data to determine at least one gene group having the characteristics same as or similar to those included in the genomic data. For example, the region-of-interest determination unit 210 may form and characterize a gene group having the same or similar characteristics by using the features annotated from the external data.

In this case, the external data may include Gene Ontology, GWAS, Biological Pathway, and the like. For example, the region-of-interest determination unit 210 may form and characterize a gene group by classifying genes using a biological process, a molecular function, a cellular component of Gene Ontology, and the like. As another example, the region-of-interest determination unit 210 may form and characterize a gene group by classifying genes using pathway data such as Kyoto Encyclopedia of Genes and Genomes (KEGG) Pathway, BioCarta, Pathway Interaction Database, Reactome and Signaling Gateway, Molecular Signature Database, and the like. As another example, the region-of-interest determination unit 210 may use any database capable of forming a set of genes, such as diseases, protein characteristics, locations of expression tissues, phenotypes, and the like.

The region-of-interest determination unit 210 may determine the region of interest from the genomic data based on biological knowledge (e.g., information on biological causal relationship) related to the genomic data. For example, the region-of-interest determination unit 210 may determine the region of interest from the genomic data based on a pathogenicity prediction, such as a SIFT score describing an evolutionarily conserved genetic feature, a PolyPhen score that is a value related to the structure of a protein, CADD, and the like. As another example, the region-of-interest determination unit 210 may determine the region of interest from the genomic data based on the American College of Medical Genetics and Genomics (ACMG) Guideline for utilizing the genome sequencing after sequencing, the ClinVar containing clinically important mutations, the GWAS Catalog containing a list of phenotype-related genes, and the like. Additionally or alternatively, external databases such as TALC, PharmGKB, ClearityFoundationBiomarkers, MyCancerGenome, TdgClinicalTrial, ClearityFoundationClinicalTrial, OncoKB, CKB, star allele nomenclature, GuideToPharmacologyInteractions, CGI, CIViC, TEND, DrugBank, DoCM, CancerCommons, TTD, FDA, and the like may be used for determining from the genomic data the relationship with the drug given to the patient. Then, the region-of-interest determination unit 210 may determine the region of interest in the genomic data based on this relationship.

In an embodiment, the region-of-interest determination unit 210 may integrate multiple genomic data (multi-omics data) to determine a feature point (that is, region of interest). For example, the region-of-interest determination unit 210 may preprocess the data using machine learning techniques such as unsupervised learning, graph structure, deep-learning, and the like in order to process different omics data such as DNA, RNA, and epigenome at once. Additionally or alternatively, the region-of-interest determination unit 210 may assign information on the same gene and construct the data in a three-dimensional form to use it as integrated data. For this, techniques such as Tensor decomposition, Single value decomposition, Matrix factorization, Uniform Manifold Approximation and Projection (UMAP), t-Stochastic Nearest Neighbor (t-SNE), Principal Component Analysis (PCA) may be used. Additionally or alternatively, the region-of-interest determination unit 210 may optionally transform the data using the machine learning technique such as deep-learning and the like. For example, by using a methodology to reduce the dimensions of each data by using autoencoder-based data, or by learning a deep-learning model to predict the same label for each data, the feature point (i.e., the region of interest) may be determined in a desired shape in a layer corresponding to a subnetwork.

The region-of-interest determination unit 210 may determine the region of interest from the genomic data by using machine learning. The genomic data may have many more features as compared to the number of samples. Accordingly, when there is no feature that can be determined as a biomarker, the region-of-interest determination unit 210 may determine the region of interest from the genomic data by using the machine learning.

In an embodiment, the region-of-interest determination unit 210 may determine the region of interest from the genomic data by using a statistical model. For example, the region-of-interest determination unit 210 may determine the region of interest in DNA data in units of mutations and/or genes. That is, based on the mutation data of DNA, the region-of-interest determination unit 210 may determine a DNA-based region of interest by performing an analysis such as statistical tests, frequency tests through contingency (e.g., Chisquare statistics, ANOVA, Fisher exact test, and the like), regression-based analysis (e.g., logistic regression, lasso, ridge, Elastic-Net), Cochrane statistics, and RVIS score for grouping and analyzing mutations in genomic units, Burden test, SKAT test, SKAT-O test, and the like.

As another example, by using a value obtained by quantifying gene expression, the region-of-interest determination unit 210 may determine a gene that is statistically and differentially expressed in RNA (Transcriptomics) data as the region of interest. The region-of-interest determination unit 210 may determine the region of interest by performing differential expression genomic (DEG) analysis of the EdgeR, the Limma, the Bayesian, or the like. Alternatively, the region-of-interest determination unit 210 may determine the region of interest by using the statistical test, regression, or machine learning technique. In this example, the transcriptomics data may include not only mRNA, but also microRNA, miRNA, and the like.

To this end, the region-of-interest determination unit 210 may use data of a structure level, such as Copy Number Alteration. For example, deletion and amplification can be defined as events and used as a categorical variable (e.g., analysis such as DNA), or the number of copy numbers can be defined and used as a continuous variable. (e.g., RNA-like analysis). Additionally or alternatively, the region-of-interest determination unit 210 may analyze epigenomics data such as methylation, histone-modification, and the like, microbiome data, and the like in the same manner as described above.

In another embodiment, the region-of-interest determination unit 210 may determine the region of interest based on the deep learning. Algorithms (e.g., ANN, DNN, CNN, Auto-Encoder) that predict results based on input data can perform the feature selection and prediction through multi-layers at once according to weights. Accordingly, the dimensions of input data (that is, genomic data) and/or features may be reduced. For example, by simply reducing the number of units of the layer, the dimensions of input data and/or features may be reduced. Accordingly, the region-of-interest determination unit 210 may use ANN, DNN, and CNN to transform the data given from the sample and select only the important features, thereby determining a new region of interest. As another example, the region-of-interest determination unit 210 may use an auto-encoder-based algorithm to reduce the dimensions of input data and/or features and efficiently determine the region of interest. That is, the region-of-interest determination unit 210 may reduce the dimensions of input data and/or features by assuming a specific distribution through a latent layer of the variational auto-encoder and the like and determine the region of interest.

As another example, the region-of-interest determination unit 210 may adjust the layer through external data to determine the region of interest. For genomic data, features listed in vectors can be set as a single gene group through units such as genomic units, chromosome units, motifs, open reading frames, and the like. In this case, each feature may belong to multiple gene groups. Therefore, when forming a layer, a method of generating new layer units as many as the number of each gene group and associating features corresponding to each gene group may be used, such that the region-of-interest determination unit 210 can extract an explainable region of interest based on medical knowledge. In this case, each group may include Gene Ontology, GWAS, Biological Pathway, and the like.

As another example, the region-of-interest determination unit 210 may determine the region of interest based on a genetic interaction. Negative genetic interactions may include relationships between genes, such as synthetic lethality, synthetic dosage lethality, synthetic cytotoxicity, and the like. In this case, genes can be utilized as independent variables, but since they form a network dependent on each other, a new region of interest may be determined through a multi-feature form. In this case, based on regression/chi-square statistics for multiple variables, a significant variable may be extracted and the region of interest may be determined.

Figure 6:
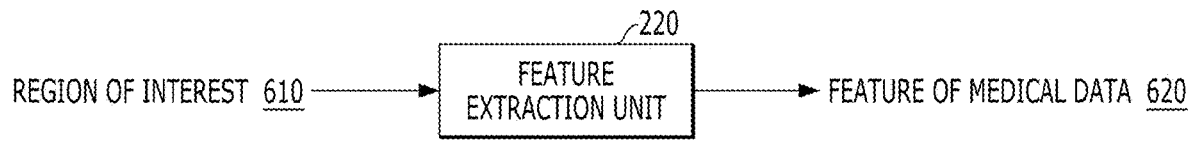
FIG. 6 is a diagram illustrating an example of extracting a feature of medical data (e.g., a feature associated with medical data) from a region of interest according to an embodiment.

FIG. 6 is a diagram illustrating an example of extracting a feature 620 of medical data (e.g., a feature associated with medical data) from a region of interest 610 according to an embodiment. As illustrated, the feature extraction unit 220 may extract one or more features 620 associated with the medical data based on the determined region of interest 610. In an embodiment, the feature extraction unit 220 may extract the one or more features 620 from the region of interest 610 based on the medical information. In this case, in performing the medical prediction, the one or more features 620 may include meaningful anatomical feature, geometric feature, or histological feature. For example, the one or more features 620 may include features necessary to perform a specific medical prediction according to a medical causal relationship that was already established.

In an embodiment, the feature extraction unit 220 may extract the one or more features 620 associated with the medical data by detecting one or more target items included in the region of interest 610 (e.g., biological components including cancer cells, immune cells, fibroblasts, lymphocytes, plasma cells, macrophage, endothelial cells, cancer areas, cancer stroma areas, tertiary lymphoid structure, normal region, necrosis, fat, blood vessel, high endothelial venule, lymphatic vessel, nerve, and the like). To this end, the feature extraction unit 220 may detect one or more target items included in the region of interest 610 using a target item detection model (e.g., a recognition model). Additionally or alternatively, the user may directly detect one or more target items in the region of interest 610, and the feature extraction unit 220 may receive the result of the target item detection input from the user.

Then, the feature extraction unit 220 may calculate independent or interdependent statistical values and/or measurements based on the detection result of one or more target items in the region of interest 610. For example, the feature extraction unit 220 may calculate the average number of cancer cells per unit area of the cancer epithelium region, which is the region of interest, as the feature 620 of the corresponding medical data (that is, one or more features associated with the medical data). As another example, the feature extraction unit 220 may calculate the average number of immune cells per unit area of the cancer stroma region in the region of interest 610, statistics on the distances between the plurality of immune cells and the plurality of cancer cells, and the like as the feature 620 of the medical data. As another example, the feature extraction unit 220 may extract the number and locations of nodules in the lung region that is the region of interest, as the feature 620 of the corresponding medical data. Additionally or alternatively, the feature extraction unit 220 may extract a set of statistical values and/or measurements calculated as described above as the feature 620 of the medical data.

In another embodiment, the feature extraction unit 220 may extract the one or more features 620 from the region of interest 610 using a pre-trained model (e.g., a pre-trained network). In this case, the pre-trained model (e.g., pre-trained CNN) may include a model (e.g., ImageNet-pre-trained model) trained based on medical data in the form of an image (e.g., medical image data related to medical imaging, tissue image data, and the like). Additionally or alternatively, the pre-trained model may include a model trained based on medical data (e.g., genomic data, biological data, and the like) that is not in the form of an image.

For example, the feature extraction unit 220 may input the region of interest 610 (e.g., an image corresponding to the region of interest) into the pre-trained model to extract an output of mid-level representation (e.g., feature map) as the one or more features 620. As another example, the feature extraction unit 220 may divide the region of interest into a plurality of regions, and input the plurality of divided regions into a pre-trained model to obtain a mid-level representation. Then, the feature extraction unit 220 may aggregate the obtained mid-level representations into one fixed-dimensional vector to extract the one or more features 620. In this case, the feature extraction unit 220 may perform aggregation using average pooling, max pooling, BOW, VLAD, Fisher Kernel, and the like.

Additionally or alternatively, with respect to the first and second medical data belonging to categories different from each other, the feature extraction unit 220 may extract one or more features associated with the second medical data based on the region of interest determined from the first medical data. In this case, the categories may be those that are generated by classifying a plurality of medical data based on data type, type, associated disease, associated region (e.g., lung region, brain region, DNA nucleotide sequence of a specific section, and the like), data generation time, method, and the like. For example, the feature extraction unit 220 may extract, from the second medical data (e.g., genomic data, and the like), one or more features associated with the second medical data from a region corresponding to the region of interest of the first medical data (e.g., image data, and the like). Additionally or alternatively, the feature extraction unit 220 may extract, from the medical data, the data corresponding to the region of interest 610 as the one or more features 620 associated with the medical data.

Figure 7:
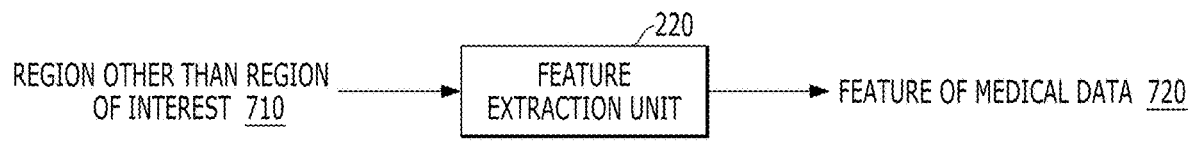
FIG. 7 is a diagram illustrating an example of extracting a feature of medical data (e.g., a feature associated with medical data) from a region other than a region of interest according to an embodiment.

FIG. 7 is a diagram illustrating an example of extracting a feature 720 of medical data (e.g., a feature associated with the medical data) from a region 710 other than a region of interest according to an embodiment. The regions other than the region of interest defined based on an already established medical causal relationship or the region of interest defined using a machine learning model may also include a significant feature for performing a medical prediction. In particular, in the case of genomic data, when a specific event occurs very rarely, since it is difficult to have statistical significance, it may not be determined as a region of interest even though it is an important factor. In addition, considering possible presence of mutations in non-coding regions and the like which may affect the medical prediction through regulatory networks, it may be important to utilize data from non-region of interest. Therefore, in order to generate a more accurate medical prediction, features extracted from regions other than the region of interest may also be used in the final training of the biomarker.

As illustrated, the feature extraction unit 220 may extract the one or more features 720 associated with the medical data based on the region 710 other than the region of interest. In an embodiment, the feature extraction unit 220 may extract the one or more features 720 (e.g., one or more second features) associated with the medical data from at least a portion of the region 710 (e.g., non-region of interest) other than the region of interest. For example, the feature extraction unit 220 may apply the process of extracting one or more features (e.g., one or more first features) from the region of interest in FIG. 6 to the non-region of interest 710 as well to extract one or more second features.

When the medical data corresponds to image data (e.g., medical image data, and the like), the feature extraction unit 220 may input the non-region of interest 710 (e.g., at least the portion of the region other than the region of interest) into a pre-trained model (e.g., a pre-trained CNN) to extract an output of mid-level representation (e.g., feature map) as the one or more features 720 associated with the medical data. Additionally or alternatively, the feature extraction unit 220 may divide the non-region of interest 710 into a plurality of regions, and may input the plurality of divided regions into the pre-trained model to obtain the mid-level representations. Then, the feature extraction unit 220 may aggregate the obtained mid-level representations into one fixed-dimensional vector to extract the one or more features 720. In this case, the feature extraction unit 220 may perform aggregation using average pooling, max pooling, BOW, VLAD, Fisher Kernel, and the like.

When the medical data corresponds to the genomic data, the feature extraction unit 220 may extract the one or more features 720 associated with the corresponding genomic data from the non-region of interest 710 having no statistical significance in the genomic data. Since there are numerous factors that correspond to the non-region of interest 710, it may be important to reduce the dimensions of data corresponding to the non-region of interest. Accordingly, the feature extraction unit 220 may reduce the dimensions within the data itself in unsupervised way by using PCA, tSNE, UMAP techniques, and the like. Additionally or alternatively, the feature extraction unit 220 may encode information through an auto-encoder or extract information from an intermediate latent layer for training a classifier to reduce the dimensions of data.

Figure 8:
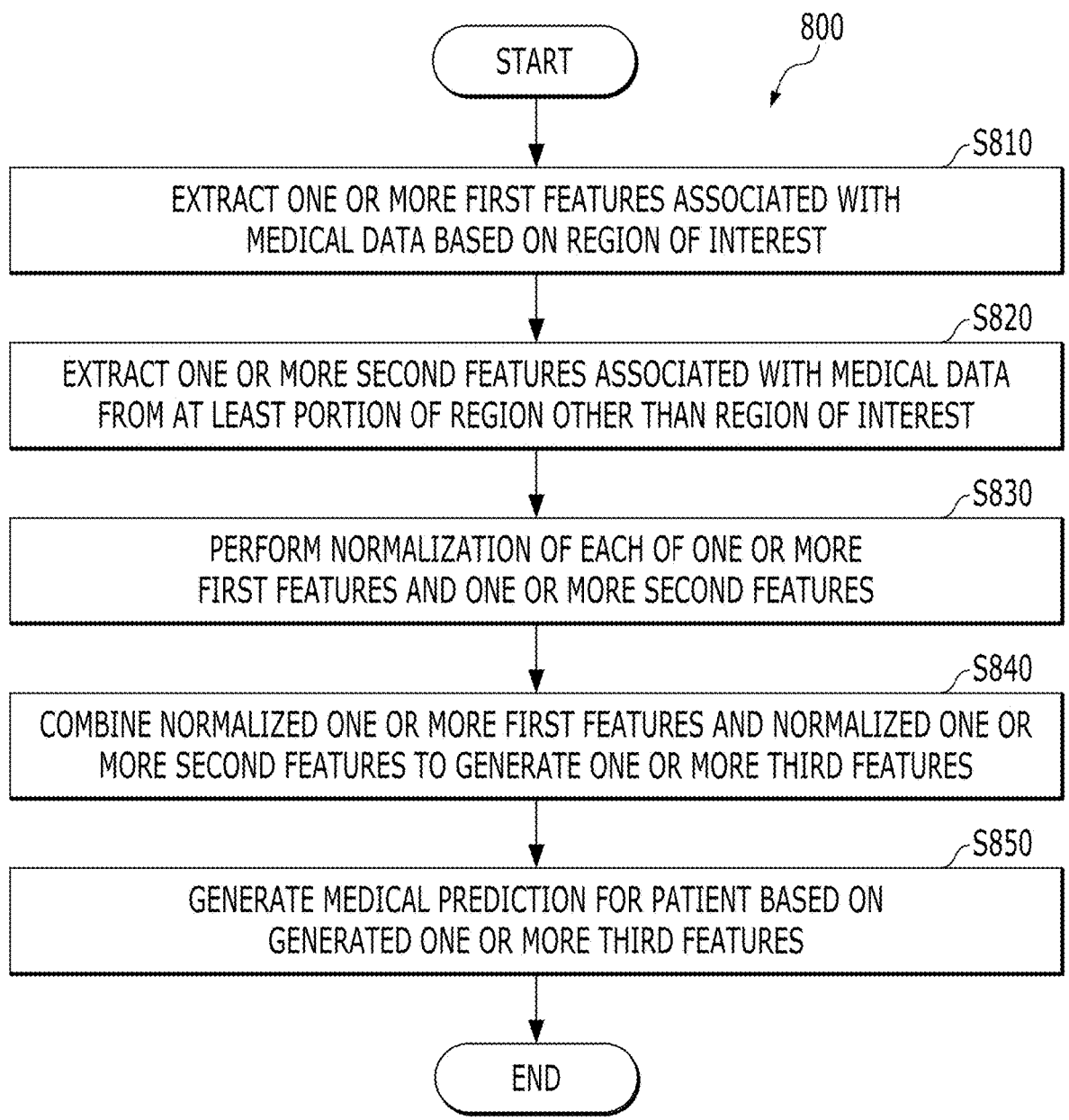
FIG. 8 is a flowchart illustrating a method for generating a medical prediction according to another embodiment.

FIG. 8 is a flowchart illustrating a method 800 for generating a medical prediction according to another embodiment. In an embodiment, the method 800 for generating a medical prediction may be performed by a processor (e.g., at least one processor of the information processing system and/or at least one processor of the user terminal). In order to generate a medical prediction, the processor may extract one or more first features associated with the medical data based on the region of interest in the medical data, at S810. In addition, the processor may extract one or more second features associated with the medical data from at least a portion of the region (e.g., the non-region of interest) other than the region of interest, at S820.

Then, the processor may perform normalization of each of the one or more first features and the one or more second features at S830, and combine the normalized one or more first features and the normalized one or more second features to generate one or more third features at S840. For example, the processor may perform L2-normalization or L1-normalization of each of one or more first features extracted from the region of interest and one or more second features extracted from the non-region of interest. Additionally or alternatively, the processor may multiply the normalized one or more first features and the normalized one or more second features by an appropriate scalar weight before combining them, to thus adjust the influence on generating a medical prediction. For example, in generating a medical prediction, a third feature may be generated by applying a scalar weight such that the one or more first features extracted from the region of interest have a greater effect than the one or more second features extracted from the non-region of interest. Then, the processor may generate a medical prediction for the patient based on the generated one or more third features at S850.

Figure 9:
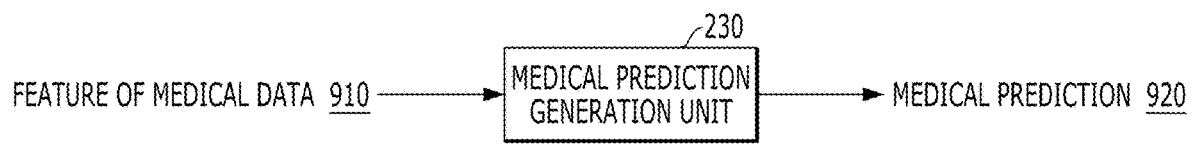
FIG. 9 is a diagram illustrating an example of generating a medical prediction based on features of medical data according to an embodiment.

FIG. 9 is a diagram illustrating an example of generating a medical prediction 920 based on a feature 910 of the medical data according to an embodiment. As illustrated, the medical prediction generation unit 230 may generate and output the medical prediction 920 for the patient based on the extracted features 910 of the medical data (that is, one or more features associated with the medical data). In an embodiment, the medical prediction generation unit 230 may generate a medical prediction for the patient based on the one or more first features and the one or more second features. For example, the medical prediction generation unit 230 may generate the medical prediction 920 for the patient based on the one or more third features.

In an embodiment, the medical prediction generation unit 230 may generate the medical prediction 920 for the patient by using a medical prediction model. For example, the medical prediction generation unit 230 may input the extracted features 910 of the medical data (that is, the one or more features associated with the medical data) into the medical prediction model to generate the medical prediction 920 (e.g., the patient's clinical histological/histologic prediction values, and the like). In this case, the medical prediction model may be a model (e.g., an artificial neural network model, a statistical model, and the like) that is trained to generate a reference medical prediction as features of reference medical data are input.

Additionally or alternatively, the medical prediction model may correspond to a model supervised by a training data set that includes a set of features extracted from the patient's medical data, an external database that can integrate external knowledge into the patient's genomic data, the patient's clinical/histological label (e.g., whether malignant or benign, recurrence or non-recurrence, metastasis or non-metastasis, response or non-response to specific anticancer drug, side effect or no side effect to drugs, effect or no effect of specific surgery, prognosis, quality of life, pain, and the like), and the like. Additionally or alternatively, the training data set of the medical prediction model may include medical data associated with a specific patient, features extracted from the medical data associated with the specific patient, a treatment method for a specific disease, therapeutic drug, treatment period, and the like. Additionally or alternatively, the training data set of the medical prediction model may include therapeutic responsiveness of the specific patient with respect to at least one of a specific treatment method or a specific therapeutic drug, chance of survival, and the like.

In an embodiment, the medical prediction generation unit 230 may generate a prediction result for at least one of a treatment method, a therapeutic drug, or a treatment period related to the patient's disease. In another embodiment, the medical prediction generation unit 230 may generate a prediction result for at least one of the patient's therapeutic responsiveness or the patient's survival rate (e.g., treatability or survivability) for at least one of a specific treatment method or a specific therapeutic drug. For example, the medical prediction generation unit 230 may generate a prediction value for the responsiveness to a drug, a prediction value for the responsiveness to administration of an anticancer drug before/after surgery, and the like as a prediction result.

The medical prediction generation unit 230 may output the generated medical prediction 920 and/or the medical prediction result. Additionally or alternatively, the medical prediction generation unit 230 may output intermediate results (e.g., an analysis result of the region of interest, and the like) generated in the process of generating the medical prediction 920. For example, the medical prediction generation unit 230 may output a heatmap of the region of interest, a detection result of a target item (e.g., a cell, a cancer region, and the like), and the like. Additionally or alternatively, the medical prediction generation unit 230 may output prediction values having various clinical utility. For example, the medical prediction generation unit 230 may output a prediction value for the responsiveness to a drug, a prediction value for the responsiveness to administration of an anticancer drug before/after surgery, and the like.

In an embodiment, the medical prediction generation unit 230 may indicate at least one of the determined region of interest, the one or more extracted features, or the generated medical prediction in the medical data. In this case, the medical prediction generation unit 230 may output the medical data (e.g., medical image data, and the like) indicating at least one of the region of interest, the one or more features, or the medical prediction. For example, the medical prediction generation unit 230 may mutually indicate on the medical data the factors that affect the medical prediction. In the case of a radiology image, the medical prediction generation unit 230 may output a heatmap or a shape and/or intensity of factors affecting the medical prediction. In the case of a pathology image, the medical prediction generation unit 230 may output a cellular-level prediction result in the form of a point at the center point of a cell nucleus, an object representing a structure such as a blood vessel or a nerve in the form of a contour, a cancerous region and/or a normal region in the form of a segmentation map, overlain on the medical data. That is, the medical prediction generation unit 230 may visualize and output the factors and/or target items that affect the medical prediction.

Additionally or alternatively, the medical prediction generation unit 230 may output information (e.g., distribution, numerical value, and the like) associated with these factors and/or target items. For example, the medical prediction generation unit 230 may output various numerical values (e.g., a density value of immune cells in a cancer region, and the like) calculated based on the detection result of the target item. As another example, when the information associated with the factors and/or target items corresponds to a graph structure, the medical prediction generation unit 230 may output the corresponding information in the form of a graph. As another example, the medical prediction generation unit 230 may output a report including the information associated with these factors and/or target items.

Figure 10:
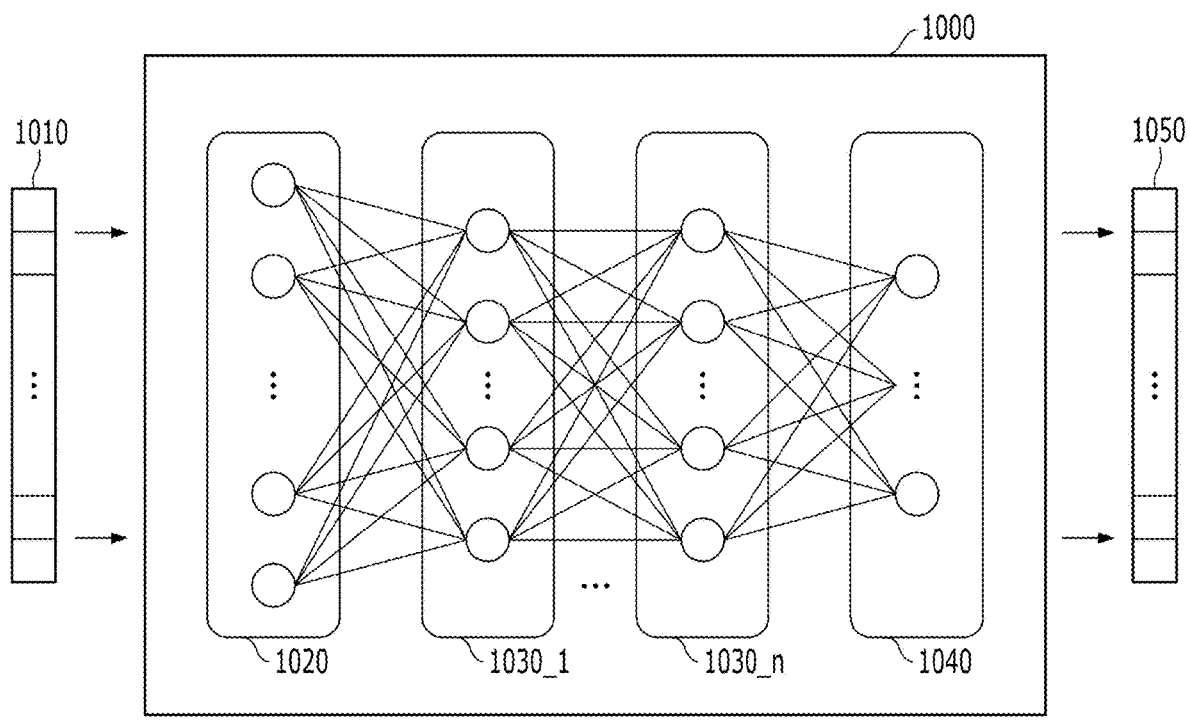
FIG. 10 is an exemplary diagram illustrating an artificial neural network model according to an embodiment.

FIG. 10 is an exemplary diagram illustrating an artificial neural network model 1000 according to an embodiment. In machine learning technology and cognitive science, an artificial neural network model 1000 as an example of the machine learning model refers to a statistical learning algorithm implemented based on a structure of a biological neural network, or to a structure that executes such algorithm.

According to an embodiment, the artificial neural network model 1000 may represent a machine learning model that obtains a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 1000 may include any probability model, neural network model, and the like, that is used in artificial intelligence learning methods such as machine learning and deep learning.

According to an embodiment, the artificial neural network model 1000 may include an artificial neural network model configured to extract at least one of the anatomical feature, the geometric feature, or the histological feature from input medical data. Additionally or alternatively, the artificial neural network model 1000 may include an artificial neural network model configured to extract one or more features associated with the medical data based on at least a portion (e.g., region of interest and/or non-region of interest) of the region of the input medical data. Additionally or alternatively, the artificial neural network model 1000 may include an artificial neural network model configured to generate a medical prediction for a patient based on one or more features associated with the input medical data (e.g., features of the medical data).

The artificial neural network model 1000 is implemented as a multilayer perceptron (MLP) formed of multiple nodes and connections between them. The artificial neural network model 1000 according to an embodiment may be implemented using one of various artificial neural network model structures including the MLP. As shown in FIG. 10, the artificial neural network model 1000 includes an input layer 1020 to receive an input signal or data 1010 from the outside, an output layer 1040 to output an output signal or data 1050 corresponding to the input data, and (n) number of hidden layers 1030_1 to 1030_n (where n is a positive integer) positioned between the input layer 1020 and the output layer 1040 to receive a signal from the input layer 1020, extract the features, and transmit the features to the output layer 1040. In an example, the output layer 1040 receives signals from the hidden layers 1030_1 to 1030_n and outputs them to the outside.

The method of training the artificial neural network model 1000 includes the supervised learning that trains to optimize for solving a problem with inputs of teacher signals (correct answers), and the unsupervised learning that does not require a teacher signal. In an embodiment, the information processing system may train the artificial neural network model 1000 by supervised learning and/or unsupervised learning to extract at least one of the anatomical feature, the geometric feature, or the histological feature from the medical data. For example, the information processing system may train the artificial neural network model 1000 by supervised learning to extract at least one of a reference anatomical feature, a reference geometric feature, or a reference histological feature from reference medical data.

In another embodiment, the information processing system may train the artificial neural network model 1000 by supervised learning and/or unsupervised learning to extract one or more features associated with the medical data based on at least a portion of the region of the medical data. For example, the information processing system may train the artificial neural network model 1000 by supervised learning to extract one or more reference features associated with the reference medical data from at least a portion of the region of the reference medical data.

In another embodiment, the information processing system may train the artificial neural network model 1000 by supervised learning and/or unsupervised learning to generate a medical prediction for a patient based on one or more features associated with the medical data. For example, the information processing system may train the artificial neural network model 1000 by supervised learning so that the artificial neural network model 1000 outputs a reference medical prediction as one or more features associated with the reference medical data (e.g., features of the reference medical data) are input.

The artificial neural network model 1000 trained as described above may be stored in a memory (not illustrated) of the information processing system, and may extract at least one of the anatomical feature, the geometric feature, or the histological feature in response to an input of the medical data received from the communication module and/or the memory. Additionally or alternatively, the artificial neural network model 1000 may extract one or more features associated with the medical data in response to an input of at least a portion of the region of the medical data.

According to an embodiment, an input variable of the artificial neural network model for extracting at least one of the anatomical feature, the geometric feature, or the histological feature may be medical data (e.g., image data, genomic data, and the like). For example, the input variable input to the input layer 1020 of the artificial neural network model 1000 may be a vector 1010 that is the medical data configured as one vector data element. In response to the input of the medical data, an output variable output from the output layer 1040 of the artificial neural network model 1000 may be a vector 1050 representing or characterizing at least one of the anatomical feature, the geometric feature, or the histological feature. That is, the output layer 1040 of the artificial neural network model 1000 may be configured to output a vector representing or characterizing at least one of the anatomical feature, the geometric feature, or the histological feature. In the present disclosure, the output variable of the artificial neural network model 1000 is not limited to the type described above, and may include any information or data that indicates at least one of the anatomical feature, the geometric feature, or the histological feature. In addition, the output layer 1040 of the artificial neural network model 1000 may be configured to output a region that has a great influence on extracting at least one of the anatomical feature, the geometric feature, or the histological feature from the medical data.

In another embodiment, the input variable of the machine learning model for extracting one or more features associated with medical data, that is, the input variable of the artificial neural network model 1000 may be at least a portion (e.g., region of interest and/or non-region of interest) of the region of the medical data. For example, the input variable input to the input layer 1020 of the artificial neural network model 1000 may be the vector 1010 that is at least a portion of the region of medical data configured as one vector data element. In response to the input of at least a portion of the region of the medical data, the output variable output from the output layer 1040 of the artificial neural network model 1000 may be the vector 1050 representing or characterizing one or more features associated with the medical data. In the present disclosure, the output variable of the artificial neural network model 1000 is not limited to the type described above, and may include any information or data that indicates one or more features associated with the medical data.

In still another embodiment, the input variable of the machine learning model for generating the medical prediction, that is, the input variable of the artificial neural network model 1000 may be one or more features associated with the medical data (e.g., features of the medical data). For example, the input variable input to the input layer 1020 of the artificial neural network model 1000 may be the vector 1010 including one or more features associated with the medical data are configured as one vector data element. In response to the input of one or more features associated with the medical data, the output variable output from the output layer 1040 of the artificial neural network model 1000 may be the vector 1050 representing or characterizing a medical prediction for the patient. The output variable of the artificial neural network model 1000 is not limited to the type described above, and may include any information or data that indicates a medical prediction for the patient.

As described above, the input layer 1020 and the output layer 1040 of the artificial neural network model 1000 are respectively matched with a plurality of output variables corresponding to a plurality of input variables, and the synaptic values between nodes included in the input layer 1020, the hidden layers 1030_1 to 1030_n, and the output layer 1040 are adjusted, so that by training, a correct output corresponding to a specific input can be extracted. Through this training process, the features hidden in the input variables of the artificial neural network model 1000 may be confirmed, and the synaptic values (or weights) between the nodes of the artificial neural network model 1000 may be adjusted so as to reduce the errors between the output variable calculated based on the input variable and the target output. The artificial neural network model 1000 trained as described above may output at least one of the anatomical feature, the geometric feature, or the histological feature in response to the input medical data. Additionally or alternatively, the artificial neural network model 1000 may output one or more features associated with the medical data in response to at least a portion of the region of the input medical data. Additionally or alternatively, the artificial neural network model 1000 may generate a medical prediction for the patient in response to one or more features associated with the input medical data.

Figure 11:
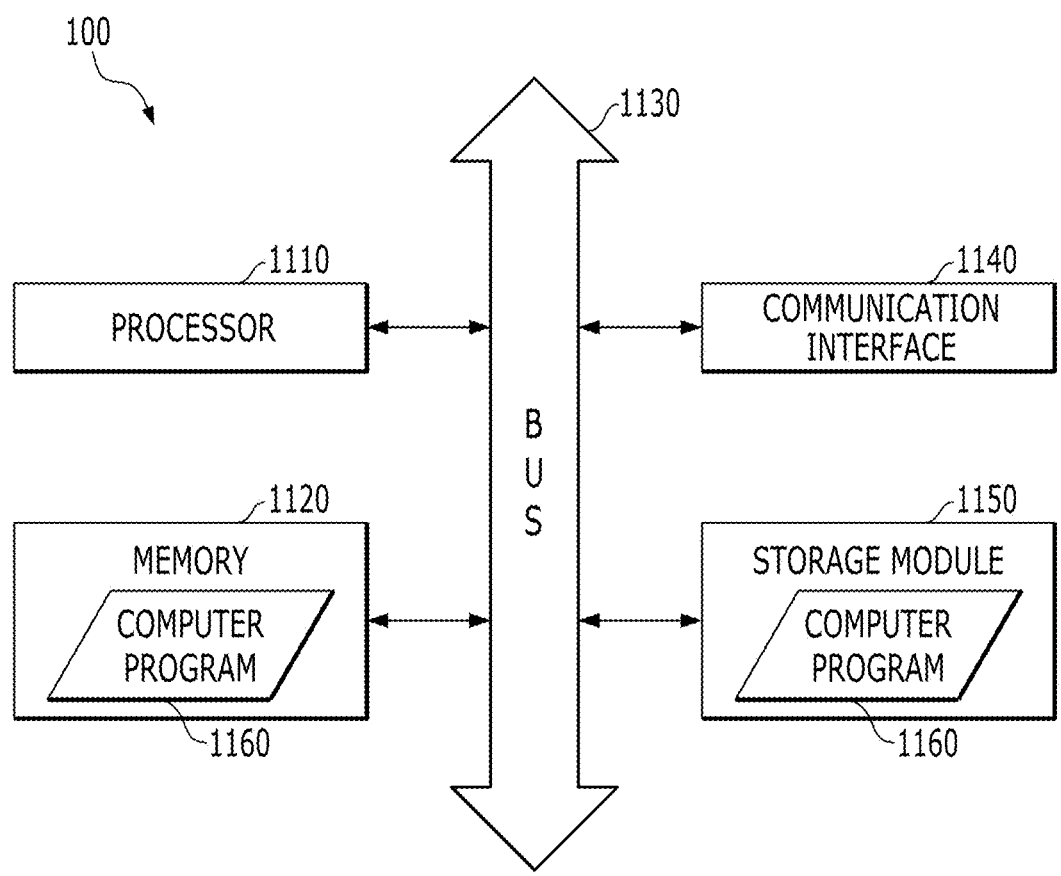
FIG. 11 is a block diagram illustrating an information processing system for generating a medical prediction related to a biomarker from medical data according to an embodiment.

FIG. 11 is a block diagram illustrating the information processing system 100 for generating a medical prediction related to a biomarker from the medical data according to an embodiment. As illustrated, the information processing system 100 may include one or more processors 1110, a bus 1130, a communication interface 1140, a memory 1120 for loading a computer program 1160 to be executed by the processors 1110, and a storage module 1150 for storing the computer program 1160. However, only the components related to the embodiment of the present disclosure are illustrated in FIG. 11. Accordingly, those of ordinary skill in the art to which the present disclosure pertains will be able to recognize that other general-purpose components may be further included in addition to the components shown in FIG. 11.

The processors 1110 control the overall operation of components of the information processing system 100. The processors 1110 may be configured to include a central processing unit (CPU), a microprocessor unit (MPU), a micro controller unit (MCU), a graphic processing unit (GPU), or any type of processor well known in the technical field of the present disclosure. In addition, the processors 1110 may perform an arithmetic operation on at least one application or program for executing the method according to the embodiments of the present disclosure. The information processing system 100 may include one or more processors.

The memory 1120 may store various types of data, commands, and/or information. The memory 1120 may load one or more computer programs 1160 from the storage module 1150 in order to execute the method/operation according to various embodiments of the present disclosure. The memory 1120 may be implemented as a volatile memory such as RAM, but the technical scope of the present disclosure is not limited thereto.

The bus 1130 may provide a communication function between components of the information processing system 100. The bus 1130 may be implemented as various types of buses such as an address bus, a data bus, a control bus, or the like.

The communication interface 1140 may support wired/wireless Internet communication of the information processing system 100. In addition, the communication interface 1140 may support various other communication methods in addition to the Internet communication. To this end, the communication interface 1140 may be configured to include a communication module well known in the technical field of the present disclosure.

The storage module 1150 may non-temporarily store one or more computer programs 1160. The storage module 1150 may be configured to include a nonvolatile memory such as a read only memory (ROM), an erasable programmable ROM (EPROM), an electrically erasable programmable ROM (EEPROM), a flash memory, and the like, a hard disk, a detachable disk, or any type of computer-readable recording medium well known in the art to which the present disclosure pertains.

The computer program 1160 may include one or more instructions that, when loaded into the memory 1120, cause the processors 1110 to perform an operation/method in accordance with various embodiments of the present disclosure. That is, the processors 1110 may perform operations/methods according to various embodiments of the present disclosure by executing one or more instructions.

For example, the computer program 1160 may include one or more instructions for causing the following operations to be performed: obtaining medical data associated with a patient, determining a region of interest in the medical data, extracting one or more features associated with the medical data based on the region of interest, and generating a medical prediction for the patient based on the extracted one or more features. In this case, a medical prediction generating system according to some embodiments of the present disclosure may be implemented through the information processing system 100.

The above description of the present disclosure is provided to enable those skilled in the art to make or use the present disclosure. Various modifications of the present disclosure will be readily apparent to those skilled in the art, and the general principles defined herein may be applied to various modifications without departing from the spirit or scope of the present disclosure. Thus, the present disclosure is not intended to be limited to the examples described herein but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

Although the present disclosure has been described in connection with some embodiments herein, it should be understood that various modifications and changes can be made without departing from the scope of the present disclosure, which can be understood by those skilled in the art to which the present disclosure pertains. In addition, such modifications and changes should be considered within the scope of the claims appended herein.

What is claimed is:

1. A method performed by at least one processor for generating a medical prediction related to a biomarker from medical data, the method comprising:
   obtaining medical data associated with a patient;
   determining a region of interest in the medical data;
   extracting one or more first features associated with the medical data based on the region of interest;
   extracting one or more second features associated with the medical data based on at least a portion of a region other than the region of interest;
   applying a weight to the one or more first features;
   generating a medical prediction for the patient based on the one or more first features to which the weight is applied and the one or more second features; and
   outputting the medical prediction.

2. The method according to claim 1, wherein the determining the region of interest includes determining the region of interest to extract at least one of an anatomical feature, a geometric feature, or a histological feature from the medical data.

3. The method according to claim 2, wherein the determining the region of interest to extract at least one of the anatomical feature, the geometric feature, or the histological feature includes determining the region of interest in the medical data by using a feature extraction model that is trained to extract at least one of the anatomical feature, the geometric feature, or the histological feature from the medical data.

4. The method according to claim 1, wherein the medical data includes genomic data, and
   the determining the region of interest includes:
      determining at least one gene group having a characteristic same as or similar to a characteristic included in the genomic data by using a database related to an interpretation of the genomic data; and
      determining the region of interest in the genomic data using the determined at least one gene group.

5. The method according to claim 1, wherein the medical data includes first medical data and second medical data belonging to different categories, and
   the extracting the one or more first features includes extracting one or more features associated with the second medical data based on the region of interest determined from the first medical data.

6. The method according to claim 1, wherein the generating the medical prediction based on the one or more first features to which the weight is applied and the one or more second features includes:
   performing normalization of each of the one or more first features to which the weight is applied and the one or more second features;
   combining the normalized one or more first features and the normalized one or more second features to generate one or more third features; and
   generating the medical prediction for the patient based on the generated one or more third features.

7. The method according to claim 1, wherein the medical data includes at least one of medical image data related to medical imaging, tissue image data, genomic data, or biological data.

8. The method according to claim 1, wherein the generating the medical prediction includes generating a prediction result for at least one of a treatment method, a therapeutic drug, or a duration of treatment related to a patient's disease.

9. The method according to claim 1, wherein the generating the medical prediction includes generating a prediction result for at least one of a therapeutic responsiveness of the patient or a survival rate of the patient for at least one of a specific treatment method or a specific therapeutic drug.

10. The method according to claim 1, further comprising indicating at least one of the region of interest, the one or more first features, the one or more second features, or the medical prediction on the medical data.

11. An information processing system comprising:
   a memory storing one or more instructions; and
   a processor configured to execute the one or more instructions to:
      obtain medical data associated with a patient;
      determine a region of interest in the medical data;
      extract one or more first features associated with the medical data based on the region of interest;
      extract one or more second features associated with the medical data based on at least a portion of a region other than the region of interest;
      apply a weight to the one or more first features;
      generate a medical prediction for the patient based on the one or more first features to which the weight is applied and the one or more second features; and
      output the medical prediction.

12. The information processing system according to claim 11, wherein the processor is further configured to determine the region of interest to extract at least one of an anatomical feature, a geometric feature, or a histological feature from the medical data.

13. The information processing system according to claim 12, wherein the processor is further configured to determine the region of interest in the medical data by using a feature extraction model that is trained to extract at least one of the anatomical feature, the geometric feature, or the histological feature from the medical data.

14. The information processing system according to claim 11, wherein the medical data includes genomic data, and
   the processor is further configured to:
      determine at least one gene group having a characteristic same as or similar to a characteristic included in the genomic data by using a database related to an interpretation of the genomic data; and
      determine the region of interest in the genomic data using the determined at least one gene group.

15. The information processing system according to claim 11, wherein the medical data includes first medical data and second medical data belonging to different categories, and
   the processor is further configured to extract the one or more first features associated with the second medical data based on the region of interest determined from the first medical data.

16. The information processing system according to claim 11, wherein the processor is further configured to:
   perform normalization of each of the one or more first features to which the weight is applied and the one or more second features;
   combine the normalized one or more first features and the normalized one or more second features to generate one or more third features; and
   generate the medical prediction for the patient based on the generated one or more third features.

17. The information processing system according to claim 11, wherein the processor is further configured to generate a prediction result for at least one of a treatment method, a therapeutic drug, or a duration of treatment related to a patient's disease.

18. The information processing system according to claim 11, wherein the processor is further configured to generate a prediction result for at least one of a therapeutic responsiveness of the patient or a survival rate of the patient for at least one of a specific treatment method or a specific therapeutic drug.

* * * * *